United States Patent
Liu (10) Patent No.: US 11,919,990 B2
(45) Date of Patent: Mar. 5, 2024

(54) ONE-POT PROCESS OF MAKING SILICONE-ACRYLIC HYBRID PRESSURE SENSITIVE ADHESIVE COMPOSITIONS

(71) Applicant: HENKEL AG & CO. KGaA, Duesseldorf (DE)

(72) Inventor: Yuxia Liu, Dayton, NJ (US)

(73) Assignee: HENKEL AG & CO. KGaA, Duesseldorf (DE)

(*) Notice: Subject to any disclaimer, the term of this patent is extended or adjusted under 35 U.S.C. 154(b) by 723 days.

(21) Appl. No.: 17/060,358

(22) Filed: Oct. 1, 2020

(65) Prior Publication Data
US 2021/0070910 A1   Mar. 11, 2021

Related U.S. Application Data

(63) Continuation of application No. PCT/US2019/032558, filed on May 16, 2019.

(60) Provisional application No. 62/672,205, filed on May 16, 2018.

(51) Int. Cl.
| | |
|---|---|
| C09J 143/04 | (2006.01) |
| A61K 9/70 | (2006.01) |
| C08F 283/12 | (2006.01) |
| C08L 83/04 | (2006.01) |
| C09J 151/08 | (2006.01) |

(52) U.S. Cl.
CPC .......... *C08F 283/12* (2013.01); *A61K 9/7061* (2013.01); *C09J 151/085* (2013.01)

(58) Field of Classification Search
CPC .............. C08F 283/12; C08F 220/1808; C08F 220/14; C08F 230/08; A61K 9/7061; A61K 9/7053; C09J 151/085; C09J 143/04; C08G 77/442; C08L 9/00; C08L 83/04
See application file for complete search history.

(56) References Cited

U.S. PATENT DOCUMENTS

| | | | |
|---|---|---|---|
| 2,676,182 A | 4/1954 | Daudt et al. | |
| 2,814,601 A | 11/1957 | Currie et al. | |
| 8,124,689 B2 | 2/2012 | Loubert et al. | |
| 8,569,416 B2 | 10/2013 | Evans et al. | |
| 8,580,891 B2 | 11/2013 | Liu et al. | |
| 8,614,278 B2 | 12/2013 | Loubert et al. | |

(Continued)

FOREIGN PATENT DOCUMENTS

| | | |
|---|---|---|
| CN | 102686629 A | 9/2012 |
| CN | 102803420 A | 11/2012 |

(Continued)

*Primary Examiner* — Ernst V Arnold
(74) *Attorney, Agent, or Firm* — Sun Hee Lehmann (57) ABSTRACT

The invention related to a one-pot process of making a single-phase silicone-acrylic hybrid adhesive composition comprising acrylic polymer and silicone polymer that are covalently bonded through a —Si—O—Si— linkage. The acrylic polymer contains at least one hydrolyzable silane (meth)acrylic monomer or siloxane (meth)acrylic macromer. These functional moieties provide reaction sites to form —Si—O—Si— bond by reacting hydrolyzable groups in the silicone polymer in the presence of a base or acid catalyst and water. The formed covalent bonds between the two incompatible systems of silicone polymer and acrylic polymer prevents phase separation and thereby a permanent, homogeneous single-phase system is formed.

20 Claims, 1 Drawing Sheet

(56) References Cited

U.S. PATENT DOCUMENTS

| | | | |
|---|---|---|---|
| 8,664,329 B2* | 3/2014 | Liu | C09J 183/00 |
| | | | 524/588 |
| 9,000,065 B2 | 4/2015 | Rashid et al. | |
| 9,856,405 B2 | 1/2018 | Ha et al. | |
| 10,463,737 B2 | 11/2019 | Huber et al. | |
| 2012/0095159 A1* | 4/2012 | Liu | C09J 133/00 |
| | | | 524/588 |
| 2015/0125413 A1 | 5/2015 | Teboul | |
| 2016/0136084 A1 | 5/2016 | Teboul | |
| 2017/0368179 A1 | 12/2017 | Huber et al. | |
| 2018/0002583 A1 | 1/2018 | Evans et al. | |

FOREIGN PATENT DOCUMENTS

| | | |
|---|---|---|
| CN | 102947370 A | 2/2013 |
| CN | 103055315 A | 4/2013 |
| CN | 107428887 A | 12/2017 |
| WO | 2010124187 A2 | 10/2010 |
| WO | 2011133408 A2 | 10/2011 |

* cited by examiner

ONE-POT PROCESS OF MAKING SILICONE-ACRYLIC HYBRID PRESSURE SENSITIVE ADHESIVE COMPOSITIONS

FIELD OF THE INVENTION

The invention relates to one-pot process of making a single-phase silicone-acrylic hybrid pressure sensitive adhesive compositions and applications thereof. The one-pot process streamlines and simplifies making the single-phase silicone-acrylic hybrid pressure sensitive adhesive compositions. The silicone-acrylic hybrid pressure sensitive adhesive compositions are particularly useful as transdermal patches to deliver pharmaceutical, nutraceutical and/or cosmeceutical agents through tissue diffusion.

BACKGROUND OF THE INVENTION

Pressure sensitive adhesives (PSA) are widely used in drug delivery systems as transdermal patches. An active(s), such as pharmaceutical, nutraceutical and/or cosmeceutical agent, is blended or dissolved in a pressure sensitive adhesive and the active is released from the adhesive to the tissue, bypassing the gastrointestinal system. The advantages of direct delivery, combined with continuous and/or controlled drug delivery, have prompted the development of new transdermal PSA compositions. The biocompatibility and inertness requirement imposed on the PSA compositions are stringent since it is necessary to avoid tissue irritation and allergic reaction. Transdermal PSA compositions remain permanently tacky at room temperature, hold the patch to the tissue with gentle pressure, and remove without causing pain or depositing adhesive residue on the tissue.

Acrylic-based pressure sensitive adhesives have been broadly used as transdermal PSA due to their low cost and good active solubility, but they are often associated with tissue irritation. Silicone-based pressure sensitive adhesives, on the other hand, exhibit excellent biocompatibility and inertness, which provide low tissue irritation; however, they have poor drug solubility. Blended hybrid adhesives of silicone and acrylic PSA have advantages of improved drug solubility and low tissue irritation; however, the physical blend of the two PSA systems is thermodynamically and kinetically unstable and quickly leads to macroscopic phase separation. The phase separation usually makes it difficult for the PSA coating process and may also change the PSA properties over time. Thus, there is an ongoing demand and continuing need for phase stable silicone-acrylic hybrid PSA compositions that have both good drug solubility and low tissue irritation. The current invention addresses this.

An attempt to overcome this incompatibility has been addressed in U.S. Pat. No. 8,124,689, 8,569,416, and 8,614,278, where an acrylic-grafted-silicone-adhesive is formed by a complex process. However, this complex process makes removal of residual monomer difficult, and the level of crosslinking cannot be well controlled. The unreacted silicone and acrylic components in the solution still lead to phase separation over time.

U.S. Pat. No. 8,580,891 provides silicone-acrylic hybrid compositions prepared by reacting silicone polymers, silicone resins, and silyl containing acrylic polymers; however, the adhesive compositions suffer short shelf-life and phase separation in less than a month.

U.S. Pat. No. 8,664,329 provides a silicone-acrylic copolymer, which comprises a covalently bonded silicone polymer with an acrylic polymer through the —Si—O—Si— linkage. The silicone-acrylic copolymer is a reaction product of (a) a silicone polymer, (b) an acrylic polymer, which comprises a silane or a siloxane functional group; and (c) a scrambling catalyst, wherein the ratio of the silicone polymer (a) and acrylic polymer (b) is from 50:1 to 1:50. The process, however, is an inefficient three step process, wherein the first step is to make acrylic polymer, and then to make silicone-acrylic hybrid copolymer in the second step, and finally in the third step to make the silicone-acrylic PSA.

There is a need in the art to have a simple, efficient, and one-pot process of making silicone-acrylic hybrid pressure sensitive adhesives. The current invention addresses this.

SUMMARY OF THE INVENTION

The present invention describes a one-pot process of making a single-phase silicone-acrylic hybrid pressure sensitive adhesive compositions and applications thereof. In one embodiment, the process comprises the steps of:
(a) making an acrylic polymer by a free radical polymerization in an organic solution;
(b) adding (i) a silicone polymer, and (ii) a catalyst into the acrylic polymer solution and reacting to form a silicone-acrylic hybrid solution;
(c) neutralizing the silicone-acrylic hybrid solution with a neutralization reagent;
(d) filtering any solid precipitates from the silicone-acrylic hybrid solution to form a single-phase silicone acrylic hybrid composition in solution;
wherein the ratio of the silicone polymer and the acrylic polymer is from 50:1 to 1:50,
wherein the silicon-acrylic hybrid composition comprises —Si—O—Si— covalent bond linkages between the silicone polymer and the acrylic polymer.

In another embodiment, the one-pot process of making a single-phase silicone-acrylic hybrid pressure sensitive adhesive composition comprises the steps of:
(a) making an acrylic polymer by a free radical polymerization of (i) a mixture of monomers, wherein at least one monomer comprises a hydrolyzable silane (meth) acrylic monomer and/or a siloxane (meth)acrylic macromer, (ii) a free radical initiator; (iii) an organic solvent, wherein the reaction temperature is from about 50 to about 150° C., and reaction time is from about 2 to 24 hr;
(b) adding (i) a silicone polymer, and (ii) a catalyst into the acrylic polymer solution and reacting at a reaction temperature of about 50 to about 150° C. for about 2 to 24 hours to form a silicone-acrylic hybrid solution;
(c) neutralizing the silicone-acrylic hybrid solution at a temperature of about room temperature to about 150° C. for about 2 to 24 hours; and
(d) filtering any solid precipitates from the silicone-acrylic hybrid solution to form a single-phase silicone acrylic hybrid composition in solution;
wherein the ratio of the silicone polymer and the acrylic polymer is from 50:1 to 1:50,
wherein the silicon-acrylic hybrid composition comprises —Si—O—Si— covalent bond linkages between the silicone polymer and the acrylic polymer.

Another embodiment is directed to making a transdermal device comprising a silicone-acrylic hybrid PSA composition and an active comprising the steps of:
(a) making an acrylic polymer solution by a polymerization reaction of (ai) a mixture of monomers, wherein at least one monomer comprises a hydrolyzable silane (meth)acrylic monomer and/or a siloxane (meth)acrylic macromer, (aii) a radical initiator; (aiii) an organic solvent, and (b) adding (bi) a silicone polymer, and (bii) a catalyst into the acrylic polymer solution (a) and reacting at a reaction temperature of about 50 to about 150° C. for about 2 to 24 hours to form a silicone-acrylic hybrid solution;

(c) neutralizing the silicone-acrylic hybrid solution at a temperature of about room temperature to about 150° C. for about 2 to 24 hours;

(d) filtering any solid precipitates from the silicone-acrylic hybrid solution to form a single-phase silicone acrylic hybrid composition in solution;

(e) adding an active to the solution, wherein the active is a pharmaceutical, nutraceutical and/or cosmeceutical agent;

(f) applying the solution onto a film; and (g) evaporating the solvent to form a transdermal device.

DETAILED DESCRIPTION OF THE INVENTION

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

As used in the specification and in the claims, the term "comprising" may include the embodiments "consisting of and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of and "consisting essentially of the enumerated ingredients/steps, which allows the presence of only the named ingredients/steps, along with any impurities that might result therefrom, and excludes other ingredients/steps.

Numerical values in the specification and claims of this application, particularly as they relate to polymers, polymer compositions or adhesive compositions, reflect average values for a composition that may contain individual polymers of different characteristics. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values). The endpoints of the ranges and any values disclosed herein are not limited to the precise range or value; they are sufficiently imprecise to include values approximating these ranges and/or values. As used herein, approximating language may be applied to modify any quantitative representation that may vary without resulting in a change in the basic function to which it is related. Accordingly, a value modified by a term or terms, such as "about," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

As used herein, a polymer or an oligomer is a macromolecule that consists of monomer units is equal or greater than about one monomer unit. Polymer and oligomer, or polymeric and oligomeric, are used interchangeably here in the invention.

As used herein, the term "alkyl" refers to a monovalent linear, cyclic or branched moiety containing C1 to C24 carbon and only single bonds between carbon atoms in the moiety and including, for example, methyl, ethyl, propyl, isopropyl, n-butyl, sec-butyl, isobutyl, tert-butyl, n-pentyl, n-hexyl, heptyl, 2,4,4-trimethylpentyl, 2-ethylhexyl, n-octyl, n-nonyl, n-decyl, n-undecyl, n-dodecyl, n-hexadecyl, and n-octadecyl.

As used herein, the term "aryl" refers to an monovalent unsaturated aromatic carbocyclic group of from 6 to 24 carbon atoms having a single ring (e.g., phenyl) or multiple condensed (fused) rings, wherein at least one ring is aromatic (e.g.,naphthyl, dihydrophenanthrenyl, fluorenyl, or anthryl). Preferred examples include phenyl, methyl phenyl, ethyl phenyl, methyl naphthyl, ethyl naphthyl, and the like.

As used herein, the term "alkoxy" refers to the group —O—R, wherein R is alkyl as defined above.

The term "silicone polymers" herein refers to (i) siloxane polymers or polydiorganosiloxanes, such as dimethylsiloxane (PDMS), methylphenylsiloxane, diphenylsiloxane, or a mixture thereof; or (ii) silicone resins, such as MQ resin, TD resin, TM resin, POSS, etc, as known in the art.

The term "one-pot process" herein refers to a reaction process and a setup including reaction flask, stirrer, condenser, etc., remain in the same configuration during the entire reaction process of making silicone-acrylic hybrid composition, and the reaction mixture is not taken out of the flask until the workup process of filtration, solvent removal or exchange, and discharge of the final product.

The "adhesive composition" herein refer to the adhesive in liquid, solution, waterborne, emulsion or hot melt form. Particularly the adhesive composition herein refers to pressure sensitive adhesive compositions or PSA compositions. As used herein, the terms "pressure sensitive adhesive" or "PSA," used interchangeably, refer to a viscoelastic material which adheres instantaneously to most substrates with an application of slight pressure and remains permanently tacky.

The invention provides a one-pot process of making single-phase silicone-acrylic hybrid pressure sensitive adhesive compositions comprising the steps of:
(a) making an acrylic polymer by a free radical polymerization in an organic solution;
(b) adding (i) a silicone polymer, and (ii) a catalyst into the acrylic polymer solution and reacting to form a silicone-acrylic hybrid solution;
(c) neutralizing the silicone-acrylic hybrid solution with a neutralization reagent;
(d) filtering any solid precipitates from the silicone-acrylic hybrid solution to form a single-phase silicone acrylic hybrid composition in solution;
wherein the ratio of the silicone polymer and the acrylic polymer is from 50:1 to 1:50,
wherein the silicon-acrylic hybrid composition comprises —Si—O—Si— covalent bond linkages between the silicone polymer and the acrylic polymer.

The silicone polymer and the acrylic polymer are covalently bonded through a —Si—O—Si— linkage. The acrylic polymer herein contains at least one silane (meth) acrylic monomer and/or a siloxane (meth)acrylic macromer, which contains hydrolyzable functional groups like Si(OR), SiOH, or Si—O—Si. These functional groups offer reaction site to form —Si—O—Si— covalent bond by reacting with SiOH in the silicone polymer in the presence of acid, base, and/or water. The covalent bond connects the incompatible silicone polymer and acrylic polymer permanently together, and prevents phase separation. The silicone-acrylic hybrid compositions may be adjusted to have adhesion properties, as known to those of skill in the art. In a particular application, the compositions will be used as PSA.

The one-pot process in the invention provides an efficient and simple method of making a complex thermal dynamically unstable system of silicone-acrylic hybrid adhesive compositions. The entire reaction process is conducted in a single reaction setting, in either chemical laboratory or in a production plant. It produces a single phase of silicone-acrylic adhesive compositions that remains in a single phase without phase separation and gelation for over six months.

The first step of the one-pot process of making silicone-acrylic PSA compositions is a free radical polymerization, where an acrylic polymer (a) is formed in an organic solvent. The acrylic polymer is made from a mixture of monomers, wherein at least one monomer is a hydrolyzable silane (meth)acrylic monomer and/or a siloxane (meth)acrylic macromer, in the presence of a free radical initiator. The polymerization temperature is from about 50 to about 150° C., and time is from about 2 to 24 hr. The weight average molecular weight (Mw) of the acrylic polymer is from about 100 to about 1,000,000 g/mol, preferably, from about 1,000 to about 100,000 g/mol.

At least one of the monomers to form the acrylic polymer is a hydrolyzable silane (meth)acrylic monomer or a siloxane (meth)acrylic macromer. The hydrolyzable silane (meth)acrylic monomer or siloxane (meth)acrylic macromer will typically be used in amounts of from 0.05 to 50 weight percent, more preferably in the range of from about 0.1 to about 20 wt % of the total weight of the acrylic polymer.

The hydrolyzable silane (meth)acrylic monomer that may be used to practice the invention has the structure of $CH_2=CHR'COO—X—SiR''_{n-3}Y_n$, wherein R' is H or methyl group; R'' is selected from the group consisting of alkyl, aryl, fluoroalkyl, trialkylsilyl, triarylsilyl, vinyl, or combination thereof; X is a linear, cyclic, or branched divalent link selected from the group of alkylene, arylene, oxyalkylene, oxyarylene, ester, amine, glycol, imide, amide, alcohol, carbonate, urethane, urea, sulfide, ether, or a derivative or combination thereof; and Y is a hydrolyzable group selected from the group consisting of alkoxy, aryloxy, acetoxy, oximino, enoxy, amino, amido, α-hydroxycarboxylic acid amide ($—OCR'_2CONR''_2$), α-hydroxycarboxylic acid ester ($—OCR'_2COOR''$), H, halogen, or combination thereof; n is selected from 1, 2, and 3. Suitable examples of hydrolyzable silane (meth)acrylic monomer that may be used to practice the invention include, but are not limited to, (meth)acryloxypropyltrialkoxysilane, (meth)acryloxypropyl alkyldialkoxysilane, and the like.

Suitable examples of siloxane (meth)acrylic macromer include, but are not limited to, mono(meth)acrylate terminated polydimethylsiloxane polymer or oligomer, e.g. trialkoxysilyl (meth)acrylates, dialkoxysilyl (meth)acrylates or methacrylates. Preferred siloxane (meth)acrylic macromers are trimethoxylsilyl and dimethoxymethylsilyl functional acrylates or methacrylates. An example of such monomer is methacryloxypropyl trimethoxylsilane. The siloxane (meth)acrylic macromer is in the content of about 0.05 to 50 wt %, based on the total weight of acrylic polymer.

The other monomers to form the acrylic polymer (a) include those having a formula of $CH_2=CR^1R^2$, wherein $R^1$ is H or methyl group; $R^2$ is selected from the group consisting of $COOR^3$ or $OCOR^3$, aryl, heterocyclic or combinations therein, wherein the $R^3$ is a linear, branched, cyclic or heterocyclic of alkyl, aryl or combination thereof; preferably, $R^3$ is selected from the group consisting of H, alkyl, aryl, allyl, fluoroalkyl, hydroxyalkyl, trialkylsilyl, triarylsilyl, epoxyalkyl, aminoalkyl, ammoniumalkyl or combination thereof.

Suitable examples of the acrylic monomers, wherein $R^1$ is H or methyl group; $R^2$ is selected from the group consisting of $COOR^3$, that may be used to practice the invention are selected from, but not limited to, a group of alkyl (meth) acrylate monomers. Preferred alkyl (meth)acrylates have up to about 48 carbon atoms in the alkyl group. These acrylic polymer components may comprise a low glass transition temperature (Tg) alkyl (meth)acrylate monomer. Low Tg monomers are those having a homopolymer Tg of less than about 0° C. Preferred low Tg alkyl (meth)acrylates for use in the invention have from about 4 to about 10 carbon atoms in the alkyl group and include methyl (meth)acrylate, ethyl (meth)acrylate, butyl (meth)acrylate, 2-ethylhexyl (meth) acrylate, isooctyl (meth)acrylate, t-octyl (meth)acrylamide, hydroxyethyl (meth)acrylate, hydroxypropyl (meth)acrylate, 2-(dimethylamino)ethyl (meth)acrylate, [2-(acryloyloxy)ethyl]trimethylammonium, (meth)acrylic acid, 2-carboxyethyl acrylate, vinyl acetate, 1-vinyl-2-pyrrolidinone, styrene, α-methylstyrene, and combinations thereof. Particularly preferred are butyl acrylate, 2-ethylhexyl acrylate and isooctyl acrylate. The low Tg acrylic monomers are preferably, but not necessarily, present in amounts greater than about 20 wt %, more typically from about 40 to about of 98 wt %, based on the total monomer weight of the acrylic polymer.

In addition, the acrylic polymer components may further comprise additional acrylic monomers having a high glass transition temperature. Non-limiting examples include methyl acrylate, ethyl acrylate, methyl methacrylate, isobutyl methacrylate and isobornyl (meth)acrylate. It will be understood by a skilled practitioner that the choice of monomers is dictated by consideration of adhesive properties, compatibility with the other adhesive matrix components, drug solubility and so forth. Thus, the monomer Tg is only one of many variables to be taken into account in any particular acrylic polymer design. Such high Tg monomers are generally used in amounts less than about 80 wt %, more typically from about 5 to about of 50 wt %, based on the total monomer weight of the acrylic polymer.

In a preferred embodiment, the acrylic polymer comprises from about 90 to about 99.5 wt % of 2-ethylhexyl acrylate and from about 0.5 to about 10 wt % of dimethoxymethylsilyl methacrylate. It has been discovered that acrylic polymers comprising greater than about 0.2 wt % of alkoxysilyl functional monomers are particularly well suited for use in hybrid adhesive compositions of the invention and can be used in the production of a single-phase stable adhesive solution.

Other useful additional acrylic monomers, if desired, may be selected from a group of carboxylic acid functional monomers. The carboxylic acids preferably contain from about 3 to about 6 carbon atoms and include, among others, acrylic acid, methacrylic acid, itaconic acid, 2-carboxyethyl acrylate and the like. Acrylic acid is particularly preferred. Such carboxy functional monomers are generally used in amounts up to about 25 wt %, more typically from about 0.5 to about of 10 wt %, based on the total monomer weight of the acrylic polymer.

In additional, functional acrylic monomers may also be added to form the acrylic polymer, and they may be selected from a group of one or more hydroxy containing functional monomers such as 2-hydroxyethyl acrylate, 2-hydroxyethyl methacrylate, hydroxypropyl acrylate, hydroxypropyl methacrylate, or combination thereof. Such hydroxy functional monomers are generally used in amounts up to about 25 wt %, more typically from about 0.5 to about of 10 wt %, based on the total monomer weight of the acrylic polymer.

Useful functional acrylic monomers may also be selected from a group of one or more N containing functional monomers. Suitable examples of the radical initiator include, but are not limited to, N-vinyl pyrrolidone, t-octyl acrylamide, N-vinyl caprolactam, N-tertiary octyl acrylamide, dimethyl acrylamide, diacetone acrylamide, N-tertiary butyl acrylamide, N-isopropyl acrylamide, cyanoethylacrylate, N-vinyl acetamide, N-vinyl formamide, 2-(dimethylamino)ethyl acrylate, [2-(acryloyloxy)ethyl] trimethylammonium chloride, or combination thereof. Such N functional monomers are generally used in amounts up to about 25 wt %, more typically from about 0.5 to about of 10 wt %, based on the total monomer weight of the acrylic polymer.

Additionally, comonomers may be added to form the acrylic polymer. Useful comonomers include vinyl acetate, styrene, α-methylstyrene, glycidyl methacrylate, epoxy-containing (meth)acrylate, allyl glycidyl ether, or combination thereof. Such comonomers are generally used in amounts up to about 25 wt %, more typically from about 0.5 to about of 10 wt %, based on the total monomer weight of the acrylic polymer.

Radical initiators are added with the acrylic monomers to form an acrylic polymer. Typical radical initiators including halogen molecules, azo compounds, or organic and inorganic peroxides can be used to make the acrylic polymer in the invention, as known to those skilled in the art, may also be selected. Suitable examples of radical initiators include, but are not limited to, 2,2'-azobisisobutyronitrile, 1,1'-azobis(cyclohexanecarbonitrile), 2,2'-azodi(2-methylbutyronitrile), 4,4-azobis(4-cyanovaleric acid), 1,1'-azobis(cyanocyclohexane), 2-2'-Azobis(2,4-dimethylvaleronitrile), 2,2-bis(tert-butylperoxy)butane, di-tert-butyl peroxide, di-tert-amyl peroxide, tert-amyl peroxypivalate, cyclohexanone peroxide, benzoyl peroxide, methyl ethyl ketone peroxide, or the like.

The acrylic polymer component of the present invention is prepared by conventional radical solution polymerization as described in the examples, while other particular polymerization methods, such as control radical polymerizations, may also be utilized. In the practice of the invention, it may also be advantageous to reduce the residual monomer content, or remove or reduce solvent levels and/or other volatiles, following polymerization using methods that are known and conventional in the art.

The polymerization reaction to make acrylic polymer is conducted in an organic solvent or co-solvents, selected from the group consisting of aliphatic hydrocarbons, aromatic hydrocarbons, ethers, acetates, ketones, alcohols, water and mixtures thereof. Preferred reaction solvents include xylene, toluene, heptane, hexane, cyclohexane, methyl cyclohexane, tetrahydrofuran, ethyl acetate, methyl ethyl ketone, acetone, isopropanol, water, and mixtures thereof. A silicone polymer may also be added as a dilute in the first step of making the acrylic polymer. Thus, the acrylic polymer component, may be formed as described as either independent of silicone polymer component, or in the presence of the silicone polymer component.

Alternatively, ready-made and commercially available acrylic polymer can also be used as either replacement or supplemental component for the acrylic polymer from in step 1. Suitable examples of such acrylic polymers are acrylic polymers comprising end-capped alkoxysilyl functional groups or polysiloxane-blocked or grafted copolymers. Examples of the end-capped alkoxysilyl functional groups are trialkoxylsilyl, dialkoxysilyl functional groups. Preferred end-capped alkoxysilyl functional groups are trimethoxylsilyl, dimethoxymethylsilyl, triethoxylsilyl and/or diethoxymethylsilyl functional groups. Suitable examples of such polymers are MS-polymer from Kaneka. Block copolymers are also useful. An example of a polysiloxane block copolymer is polydimethylsiloxane-acrylic block copolymer. The preferred amount of siloxane block is 10 to 50 wt % of the whole block polymer.

The second step of the one-pot process to make silicone-acrylic hybrid adhesive compositions is reacting the acrylic polymer solution from above step one with a silicone polymer in the presence of a catalyst. The components of the second steps are added directly into the solution, the same pot, of the acrylic polymer of the first step. The (b)(i) silicone polymer is a siloxane polymer, a silicone resin, or combination thereof. The reaction temperature is from about 50 to about 150° C., and reaction time is from about 2 to 24 hr. The ratio of the silicone polymer and the acrylic polymer is from about 50:1 to 1:50.

The (b)(i) silicone polymer that can be used in the practice of the invention include siloxane polymers that have at least two or more (R'R"SiO) unit, wherein R' and R" are independently alkyl, aryl, fluoroalkyl, trialkylsilyl, triarylsilyl, vinyl, or combination thereof. Suitable examples of siloxane polymers include polydiorganosiloxane that has terminal group selected from hydrolyzable hydroxyl, alkoxy hydride, or combination thereof, but are not limited to, are polydialkylsiloxane, polydiarylsiloxane, polyalkylarylsiloxane. In a preferred embodiment, siloxane polymers are polymers or copolymers of polydimethylsiloxane, polydiphenylsiloxane, polymethylphenylsiloxane, poly(3,3,3-trifluoropropylmethyl)siloxane, or a mixture thereof. The siloxane polymers will typically be end-capped with hydroxy, alkoxy, hydride, vinyl functional groups, and like groups. In one embodiment, end-capped functional groups are hydroxy, alkoxy, hydride functional groups, or mixtures thereof. In a most preferred embodiment, the siloxane polymer is hydroxy terminated polydimethylsiloxane (PDMS) with one or a mix of more than one average molecular weight. The weight average molecular weight of siloxane polymer will typically range from about 100 to about 3,000,000, preferably, from about 10,000 to about 350,000 g/mol.

The (b)(i) silicone polymer that can be used in the practice of the invention also include the silicone resin. The silicone resin is a network of silicone polymer that contains a combination of $R_3SiO_{1/2}$ (M unit), $R_2SiO_{2/2}$ (D unit), $RSiO_{3/2}$ (T unit) and/or $SiO_{4/2}$ (Q unit) in the cage-like chemical Si—O—Si structure. It can be made according to procedures in U.S. Pat. Nos. 2,676,182, 2,814,601 and is also obtained from various commercial sources. Preferred silicone resins are MQ, MT, TD, POSS, having independently M, D, T and/or Q units; Most preferred silicone resin is MQ resin.

The MQ resin that can be used in the practice of the invention comprises at least one tetrafunctional siloxyl unit $SiO_{4/2}$ and at least one triorganosiloxy unit $R_3SiO_{1/2}$, wherein the R is methyl, hydroxy, vinyl, phenyl, (meth)acryloxypropyl, or combination thereof, and the mole ratio of the units $SiO_{4/2}$ to $R_3SiO_{1/2}$ is from 1:2 to 2:1; wherein the R is from about 0.05 wt % to 10 wt % based on the total weight of the silicone resin; and a combination of hydroxyl and methyl groups, with 0.001 to 1 Si—OH for each Si—Me. The silicone resin has weight average molecular weight of from about 100 g/mol to 3,000,000 g/mol. Preferably from 1,000 to 100,000 g/mol. In a preferred embodiment, the silicone polymer is a combination of PDMS and MQ in a ratio ranges from about 50:1 to 1:50, most preferably, in a ratio ranges from about 9:1 to 1:9.

The (b)(ii) catalyst that can be used in the practice of the invention is either an acid or base catalyst. Preferred acid or base catalysts have a pKa value equal to or less than −6 or equal to or greater than 15 in a hydrocarbon solvent. Suitable examples of catalysts, but are not limited to, are MOR, wherein M is Cs, Rb, K, Na, Li and R is H, alkyl, aryl, allyl, fluoroalkyl, or combination thereof; organolithium reagents, Grignard reagents, methanesulfonic acid, sulfuric acid, acidic clay, Lewis acid, acidic ion exchange resins, or combination thereof. Other examples of the catalyst include Lewis acid or base, organometallic salts of metals such as tin, titanium, aluminum, bismuth. Combination of more than one type of catalysts above can also be used.

With a strong acid or base catalyst, and in the presence of water/moisture, the acrylic polymer reacts with the silicone polymer to produce a lightly crosslinked but soluble polymeric network. The reactive silyl functional monomers, once incorporated onto the acrylic polymer backbone, undergo condensation reactions with the hydroxy functional groups of the silicone polymer and fast re-equilibrated with a dynamic —Si—O—Si— bond cleavage and reformation. This step is called "a scrambling reaction," since it leads to the formation of covalent —Si—O—Si— bond completely and thus one-phase solution and polymer between otherwise the intrinsically immiscible silicone polymer and acrylic polymer. Also, the alkoxysilyl functional groups of the acrylic polymer may undergo a self-crosslinking reaction in the presence of water/moisture and the catalyst. The condensation reaction also occurs between silicone polymer molecular, particularly when more than one silicone polymers are used. While not bound to any theory, the silicone resin forms the center domain that bridges both the acrylic and siloxane polymers. These center domain forms the —Si—O—Si— linkage that forms a stable, single-phase solution adhesive with good cohesive strength.

In another embodiment, the (b)(i) silicone polymer may be added in step (a) with another acrylic monomers before the second step. The acrylic polymer may be formed in the presence of silane polymer (b). In this embodiment, the second step, step (b) would be the addition of the catalyst (b)(ii) to form the silicone-acrylic hybrid polymer.

The reaction may take place at room temperature or at an elevated temperature or up to about 180° C. The preferred temperature is in the range of about 50 to about 150° C. Typically, the reaction is from about 2 to about 24 hours. The reaction is, preferably, allowed to proceed at least until the rate of evolution of condensation byproducts, such as water, alcohol, and carbodioxide, is substantially removed. The solid content of the reaction is from about 20 to 80%, and can be adjusted by adding or removing solvent.

The third step of the one-pot process is to neutralize the solution with (c) neutralization reagents. The neutralization reagents are added into the solution, the same pot, made in the second step. The neutralization reagents that can be used in the practice of the invention are any weak organic or inorganic acid or base, either in liquid, solid, or acid/base activated clays or ion-exchange resins. Suitable examples of neutralization reagent include, but are not limited to, dilute hydrochloric acid (aq), chlorotrimethylsilane, fume silica, sodium carbonate, sodium bicarbonate, calcium carbonate, acetic acid, ammonium hydroxide(aq), ammonium carbonate, hexamethyldisilazane, aminopropyltrimethylsilane, propylene epoxide, and the like, or combination thereof. The neutralization temperature ranges from about room temperature to about 150° C., and neutralization time is from about 2 to about 24 hours.

The fourth step of the one-pot process is to filter the solution to remove any formed salts, gels, and any other solid precipitates. Filter aids, such as celite, diacel, diatomite, diatomaceous earth, and the like or combination thereof, can be used for a smooth filtration process. The remaining solution is the single-phase silicone acrylic hybrid composition. This silicone acrylic hybrid composition, as is, can be cast and dried to form a film and functions as a pressure sensitive adhesive. Occasionally, the reaction solvent may not be the one preferred in the final adhesive composition, and thus, the solvent can be removed by distillation and replaced with any other solvent or mixture of solvents before or after filtration.

The silicone-acrylic hybrid compositions may further be formulated into a variety of adhesives compositions in a form of solution adhesive, emulsion adhesive or hot melt adhesive, or be blended with additional components to form compositions such as coating, sealant, and the like. The blending may be conducted by directly adding the additional components in the solution before or after the filtration step providing the one-pot process.

The additional components are blended to achieve desired properties. Such components include, and are not limited to, tackifiers, additional polymers, silicone oils, plasticizers, diluents, solubilizing agents, organic or inorganic fillers, pigments, fluorescent additives, flow and leveling additives, wetting agents, surfactants, antifoaming agents, rheology modifiers, emulsifiers, humectants, gelling agent, colorants, other surface modifying agents, fragrances, permeation enhancers, stabilizers, antioxidants, or the like, known to those skilled in the art.

Suitable tackifiers are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; (7) mineral oils; (8) wood resins or rosins and hydrogenated forms; (9) silicone MQ, MT, TD resins or silicone oils thereof. Useful levels of tackifiers are generally from about 1 wt % to about 30 wt % based on the weight of the total composition.

The silicone-acrylic hybrid adhesive compositions of the invention may also be blended with additional polymers to enhance desired properties. Examples of polymers useful for blending include, but are not limited to, polyacrylates, polysiloxanes, polyester, polyether, polyurethane, amorphous polyalphaolefin, polyisoprene, polybutadiene, polyisobutylene, styrenic block polymers, and the like.

The silicone-acrylic hybrid adhesive compositions are particularly suitable as a transdermal adhesive film. A film is defined herein as a flexible product formed, for example, by casting, extruding or blowing, the silicone-acrylic hybrid adhesive compositions in a carrier liquid such as water or other organic solvent onto a substrate surface. A film will typically but not necessarily have a uniform thickness and will generally vary in thickness from about 0.02 mm to about 3 mm. The film can be formed or processed to have a variety of lengths, widths and shapes depending upon the desired end use application.

An active may be dissolved or blended in the solution before casting the film or dispersed on the surface of the transdermal film for delivery. In one embodiment, the active is solubilized in the silicone-acrylic hybrid adhesive composition solution at or above room temperature. The active may be first solubilized or dispersed in the solution, and then the active-containing solution or suspension is mixed with the silicone-acrylic hybrid adhesive compositions in the one-pot to form a mixture. The mixture is then coated onto a suitable substrate and dried to form a film. Alternatively, the active may be solubilized or dispersed in a solution and then sprayed or coated directly onto the cast film. The formed film comprising the active substance can be air-dried or dried under warm air to remove excess solvent. The film may then be cut to the desired dimension, packaged and stored.

The term active, also referred to herein as an active ingredient, is used to mean any "pharmaceutical," "nutraceutical" or "cosmeceutical" agent. The active ingredient may or may not be pharmacologically active, but will typically have at least a perceived therapeutic effect.

Pharmaceuticals actives that can be administered using this invention include prescription, (Rx), including controlled substances, and over-the-counter (OTC) drugs. Non-limiting classes of pharmaceutically active agents include, α-adrenoreceptor agonists, β-adrenoreceptor agonists, α-adrenoreceptor blockers, β-adrenoreceptor blockers, anabolics, analgesics (narcotics and non-narcotics), androgens, anesthetics, antiallergics, antiandrogens, antianginals, antiarrhythmics, antidiabetics, antihistamics, anti-migraine agents, bronchodialators, gestagens and vasodilators. Included are actives for diabetes, antihistamines, pain relief managements, antifungal treatments, hormone managements, sensitive teeth, acne treatments, dental and gum diseases, inflammations, antimicrobial treatments, sedation, insomnia, motion sickness, emesis, nicotine addiction, bladder control and central nervous system diseases.

Specific non-limiting examples of pharmaceuticals include insulin, loratidine, benzocaine, amlexanox, codeine, morphine, nicotine, fentanyl, miconazole, estradiol, progesterone, testosterone, potassium nitrate, salicylic acid, benzoyl peroxide, triclosan, fluoride, chorhexidine, diclofenac, ketoprophen, lidocaine and hydrocortisone.

Nutraceuticals are defined as any substance that may be considered as a food or part of food and provides medical and health benefits, including prevention and treatment of disease.

Types of nutraceutical actives that may be administered include, but are not limited to, functional foods, dietary supplements, herbal products, including antioxidants, immune enhancers, cardiovascular health enhancers, healthy joints and cartilage enhancers, memory and mental enhancers, women's health enhancers, mood and emotional enhancers, and weight loss enhancers.

Non-limiting examples of nutraceuticals include ginger, lutein, garlic, lycopene, capsaicin, caffeine, folic acid, beta-carotene, lycopene, valerian, ginseng, vitamin E, herbal teas (e.g., green tea) and natural biological flora.

It is to be understood that the above examples, including classification, are for purpose of illustration only. It will be recognized that all countries do not classify and/or regulate actives in a consistent manner. An active that treats or prevents disease, or otherwise affects the structure and/or function of the individual, may be considered to be a pharmaceutical by one country, but considered to be a cosmeceutical by another. Likewise, variations in classification exist on the cultural level as well as the individual level. What one individual may regard as a cosmeceutical, another may regard as a cosmetic agent.

It is to be understood that the above examples, including classification, are for purpose of illustration only. It will be recognized that all countries do not classify and/or regulate actives in a consistent manner. An active that treats or prevents disease, or otherwise affects the structure and/or function of the individual, may be considered to be a pharmaceutical by one country, but considered to be a cosmeceutical by another. Likewise, variations in classification exist on the cultural level as well as the individual level. What one individual may regard as a cosmeceutical, another may regard as a cosmetic agent.

Cosmeceuticals are defined as any substance or product for topical application and intended to have therapeutic effects on the body. Types of cosmeceutical actives that may be administered include, but are not limited to, moisturizers, anti-aging agents, antioxidants, self tanners, depigmenting agents, scar managements, scalp treatments, enzymes and amino acids.

Non-limiting examples of cosmeceuticals include alpha and beta hydroxy acids, glycolic acid, lactic acid, antioxidants, vitamin C, vitamin E, botanicals, papain enzyme, hydroquinone, kojic acid, thioglycolate, oatmeal and orange peel. These examples are merely illustrative since it is well known in the art that cosmecutical actives in one country are considered to be pharmaceutical actives in another.

Active loading levels for active-containing films of the invention will generally range from about 0.001 dry weight % to about 80 dry weight %, more typically from about 0.01 dry weight % to about 70 dry weight %, even more typically from about 0.01 dry weight % to about 50 dry weight %. It will be appreciated that active loading will depend on, e.g., the type of active, the size and the thickness of the film used, the individual to which the film is to be applied (human adult or child, non-human animal), etc.

The active is added in such amounts that the final active-containing single dosage form comprises a pre-determined effective amount. By effective amount is meant that the active agent is present in amounts required to impart a desired action or therapeutic dose. The active is present in an amount sufficient, also referred to herein as an effective amount, to bring about a desired result, e.g., a desired therapeutic result in the treatment of a condition. An effective amount of a drug, for example, means a nontoxic but sufficient amount of a drug to provide the selected effect over a specific predetermined period of time or number of doses. It will be appreciated that an amount that constitutes an effective amount will vary according to the particular active incorporated in the film, the condition and/or severity of the condition being treated, any other actives being co-administered with the selected active, desired duration of treatment and preferred number of dosage units, age of the individual to which the film is being administered, and the like. In this regard it is common in the medicinal art that one or two administrations are recommended, e.g., depending on body weight, age, or the like, for administration as a single dose.

In another embodiment, a further active or another active may be sprayed, sprinkled or added after the film is casted and dried.

The film may be used for both systemic and local administration of the active ingredient. The film may be used for immediate or otherwise controlled release of the active. Controlled release, as used herein, is intended to mean a method and composition for making an active ingredient available to the biological system of a host. Controlled release includes the use of instantaneous release, delayed release, and sustained release. "Instantaneous release" refers to immediate release to the biosystem of the host. "Delayed release" means the active ingredient is not made available to the host until some time delay after administration. "Sustained Release" generally refers to release of active ingredient whereby the level of active ingredient available to the host is maintained at some level over a period of time. The method of affecting each type of release can be varied.

It will be appreciated that components of the film can be selected to control the time and degree delivery of the active(s). The dimensional sizes, shape, thickness, and weight of the film will vary depending on the purpose, the site of delivery, and the individual (e.g., human, dog, horse) being treated.

The transdermal film with the active is applied to onto an individual's tissue surface. The tissue may be substantially dry or moist, such as when applied to draining wounds or serious burns. Upon contact with, the film adheres to the surface and maintains its adherence. The film has a flexible characteristic which allows the film to remain on the directed site until removed.

Tissue is used broadly herein to mean any exposed surface of an individual. By exposed surface is meant any area of the body that can be reached without an invasive (e.g., surgical) procedure. Such tissues include but are not limited to skin, various mucosal tissues (mouth, vaginal, nasal, ocular tissue, rectal), teeth, nail, and hair. The film can be applied to healthy tissues, or to damaged or irritated or diseased tissue surfaces.

The term "individual" is used herein in its broadest sense and includes animals (both human and non-human, including companion animals such as dogs, cats and horses, and livestock such as cattle and swine) and plants (both agricultural and horticultural applications).

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

EXAMPLES

Components

Silicone polymer (hydroxy terminated PDMS, Mw110,000 g/mol), 3-methacryloxypropyltrimethoxysilane, trimethoxysilane, methyldimethoxysilane are available from Gelest Inc.

2-ethyl hexyl methacrylate (2-EHA), methylacrylate (MA), 2,2'-Azobis(2-methylpropionitrile) (AIBN), heptane, xylene, acetic acid, hexamethyldisilazane, MeSiCl$_3$), (NH$_4$)$_2$CO$_3$, NH$_4$OH, KOH (1.0M), and n-butyl lithium (1.6M in hexane) were available from Sigma-Aldrich.

MQ resin is a hydroxyl functional silicone resin (Mw ~10,000 g/mol), and can be made according to procedures in U.S. Pat. Nos. 2,676,182 or 2,814,601, and can also obtained from various commercial sources, including Dow Corning, Momentive, and Wacker.

Property Testing

Shear adhesion was measured according to test method A, PSTC-107, adapted as follows. The adhesive was coated on PET (2 mil) film. The shear adhesion was measured under a shear load of 1 kg on a 12×25 mm area, applied after the adhesive film was wetting out a stainless steel panel for 15 minutes. All testing was performed at 23° C. and 50% relative humidity.

Peel adhesion at 180° was measured according to test method A, PSTC-101, adapted as follows. The adhesive was coated on PET (2 mil) film. The peel strength was measured after the adhesive film was wetting out a stainless steel panel for 15 min. All testing was performed at 23° C. and 50% relative humidity.

A Rheometrics Dynamic Mechanical Analyzer (Model RDA 700) was used to obtain the elastic moduli (G'), loss modulus (G") and tan delta versus temperature sweep. The instrument was controlled by Rhios software version 4.3.2. Parallel plates 8 mm in diameter and separated by a gap of about 2 mm were used. The sample was loaded and then cooled to about −100° C. and the time program started. The program test increased the temperature at 5° C. intervals followed by a soak time at each temperature of 10 seconds. The convection oven was flushed continuously with nitrogen. The frequency was maintained at 10 rad/s. The initial strain at the start of the test was 0.05% (at the outer edge of the plates). An autostrain option in the software was used to maintain an accurately measurable torque throughout the test. The option was configured such that the maximum applied strain allowed by the software was 80%. The autostrain program adjusted the strain at each temperature increment if warranted using the following procedure. If the torque was below 200 g-cm the strain was increased by 25% of the current value. If the torque was above 1200 g-cm it was decreased by 25% of the current value. At torques between 200 and 1200 g-cm no change in strain was made at that temperature increment. The shear storage or elastic modulus (G') and the shear loss modulus (G") are calculated by the software from the torque and strain data. Their ratio, G"/G', also known as the tan delta, was also calculated.

Example 1 (Comparative)

Preparation of Acrylic Polymer

A mixture of 2-EHA (19.6 g), trimethoxysilylpropylacrylate (0.5 g), and AIBN (0.03 g) and heptane (50 g) was charged under nitrogen to a reaction flask equipped with a stirrer, condenser, addition funnel. The mixture was heated to reflux for 15 min, and then AIBN (0.03 g) in heptane (50 g) was added over a period of 2 hr and reaction continued for 1 hr. The acrylic polymer solution was cooled to room temperature and discharged and packed in glass jar.

Example 2 (Comparative)

Preparation of Hybrid PSA 2C

In a different flask, a mixture of acrylic polymer solution from Example 1, silicone polymer (32 g), methyl MQ resin (48 g), KOH(aq) (1.0 N in water) (0.2 g), and heptane (300 g) was stirred at reflux for 4 hr. Acetic acid (0.03 g) was added and the mixture was stirred at reflux for 0.5 hr. Hexamethyldisilizane (2.0 g) was added and the reaction continued at reflux for 1 hr. The product was cooled to room temperature, filtered and packed in a glass jar. The product solution phase separated into two phases in one month.

Example 3 (Comparative)

Preparation of Hybrid PSA 3C

In a different flask, a mixture of acrylic polymer from Example 1, silicone polymer (32 g), KOH(aq) (1.0 N in water) (0.2 g), and heptane (300 g) was stirred at reflux for 4 hr. Methyl MQ resin (48 g) and $(NH_4)_2CO_3$ (1 g), $NaHCO_3$ (0.5 g) were added and the mixture was stirred at 60° C. for 3 hr and then reflux for 1 hr. Hexamethyldisilizane (2.0 g) was added and the reaction continued at reflux for 1 hr. The product was cooled to room temperature, filtered and packed in a glass jar. The product solution separated and gelled in less than 6 months.

Example 4 (Comparative)

Preparation of Hybrid PSA 4C

In a different flask, a mixture of acrylic polymer from Example 1, silicone polymer (32 g) and heptane (300 g) was stirred under nitrogen at reflux for 1 hr. n-BuLi (1.6 N in hexane, 0.3 mL) was added and mixed at reflux for 3 hr. Methyl MQ resin (48 g) was added and mixed at stirred at reflux for 1 hr, n-BuLi (1.6 N in hexane, 0.3 mL) was added and mixed at reflux for 3 hr. Hexamethyldisilizane (2.0 g) was added and the reaction continued at reflux for 1 hr. Nitrogen was turned off and $CO_2$ was introduced and reaction continued for 1 hr at reflux. The product was cooled to room temperature and packed in a glass jar. The product solution remained in one phase for more than 6 months Example 5 (Comparative)

Preparation of Acrylic-Silicone Copolymer 5C

A mixture of 2-EHA (13.5 g), MA (10 g), trimethoxysilylpropylacrylate (0.5 g), and AIBN (0.03 g) and xylene (50 g) was charged under nitrogen to a reaction flask equipped with a stirrer, condenser, addition funnel. The mixture was heated to reflux for 15 min, and then Vazo-67 (0.03 g) in xylene (50 g) was added over a period of 2 hr and reaction continued for 1 hr. Silicone polymer (Wacker Elastomer 50N, 32 g), KOH(aq) (1.0 N in water) (0.2 g), and xylene (100 g) was stirred at reflux for 4 hr. Acetic acid (0.03 g) was added and the mixture was stirred at reflux for 0.5 hr. The product was cooled to room temperature, filtered and packed in a glass jar. The product solution remained in one phase in more than 6 months.

Example 6 (Comparative)

Preparation of Hybrid PSA 6C

In a new reaction scheme, a mixture of silicone-acrylic copolymer from Example 5, methyl MQ resin (45 g), catalyst KOH (0.1 g), and xylene (30 g) was stirred at 100° C. for 3 hr. Hexamethyldisilizane (2.0 g) was added and the reaction continued for 2 hr. The product was cooled to room temperature, filtered and packed in a glass jar. The product solution stayed in one phase but gelled in less than 6 months.

Example 7 (Comparative)

Preparation of Hybrid PSA in One-Pot Method 7C

A mixture of 2-EHA (19.6 g), trimethoxysilylpropylacrylate (0.5 g), AIBN (0.03 g) and heptane (50 g) was charged under nitrogen to a reaction flask equipped with a stirrer, condenser, addition funnel. The mixture was heated to reflux for 30 min, and then AIBN (0.03 g) in heptane (50 g) was added over a period of 2 hr and reaction continued for 1 hr. silicone polymer (32 g), KOH (1.0 N in water, 0.2 g) and 200 g of heptane were added, and the mixture was stirred at reflux for 4 hr. Acetic acid (0.03 g) was added and stirred at reflux for 0.5 hr. $NH_4OH$(aq) (30% $NH_3$, 0.2 g) and methyl MQ resin (48 g) were added and the mixture was stirred at reflux for 4 hr. Hexamethyldisilizane (5.0 g) was added and the reaction continued at reflux for 1 hr. The product was cooled to room temperature, filtered and packed in a glass jar. The product solution phase-separated and gelled in less than 6 months.

Example 8 (Comparative)

Preparation of Hybrid PSA in One-Pot Method 8C

A mixture of 2-EHA (19.6 g), trimethoxysilylpropylacrylate (0.5 g), silicone polymer (32 g), AIBN (0.03 g) and heptane (50 g) was charged under nitrogen to a reaction flask equipped with a stirrer, condenser, addition funnel. The mixture was heated to reflux for 15 min, and then AIBN (0.03 g) in heptane (50 g) was added over a period of 2 hr and reaction continued for 1 hr. KOH (1.0 N in water, 0.2 g) and 200 g of heptane were added, and the mixture was stirred at reflux for 4 hr. Acetic acid (0.03 g) was added and stirred at reflux for 0.5 hr. $(NH_4)_2CO_3$ (1 g) and methyl MQ resin (48 g) were added and the mixture was stirred at 60° C. for 3 hr and then reflux for 1 hr. Hexamethyldisilizane (5.0 g) was added and the reaction continued at reflux for 1 hr. The product was cooled to room temperature, filtered and packed in a glass jar. The product solution was separated and gelled in less than 6 months.

Example 9

Preparation of Hybrid PSA in One-Pot Inventive Method 9

A mixture of 2-EHA (19.6 g), trimethoxysilylpropylacrylate (0.5 g), AIBN (0.03 g), and heptane (100 g) was charged under nitrogen to a reaction flask equipped with a stirrer and a condenser. The polymerization started by heating the mixture to reflux and hold for 1 hr. AIBN (0.03 g) was added into the same flask and mixed for 1 hr. Silicone polymer (32 g), methyl MQ resin (48 g), KOH (4 g, 1.0 N in water) and heptane (40 g) were added into the same flask and stirred at reflux for 4 hr. Trimethlchlorosilane (1 g) was added to the same flask and mixed at room temperature for 1 hr. Hexamethyldisilizane (5.0 g) was added and the reaction was heated to reflux for 2 hr. The solution was cooled to room temperature. After filtration, the hybrid PSA product was packed in a glass jar. The solution remained in one phase over 6 months.

Example 10

Preparation of Hybrid PSA in One-Pot Inventive Method 10

A mixture of 2-EHA (13 g), MA (10 g), trimethoxysilylpropylacrylate (0.5 g), silicone polymer (31 g), AIBN (0.03 g), and heptane (200 g) was charged under nitrogen to a reaction flask equipped with a mechanical stirrer and a condenser. The polymerization started by heating the mixture to reflux and hold for 1 hr. AIBN (0.03 g) was added and mixed for 1 hr. Methyl MQ resin (45 g), KOH (5 g, 1.0 N in water) and heptane (100 g) were added into the same flask and stirred at reflux for 4 hr. Trimethlchlorosilane (1 g) was added into the same flask and mixed at room temperature for 1 hr. Hexamethyldisilizane (5.0 g) was added into the same flask and the reaction was heated to reflux for 2 hr. The solution was cooled to room temperature. After filtration, the hybrid PSA product was packed in a glass jar. The solution remained in one phase over 6 months.

Example 11

Stability and Properties of Examples

| Examples | 4(C) | 6(C) | 7(C) | 8(C) | 9 | 10 |
|---|---|---|---|---|---|---|
| Phase stability, months | >6 | >6 | <6 | <6 | >6 | >6 |
| Shelf stability, months | >6 | <6 | <6 | <6 | >6 | >6 |
| Shear, SS 4.4 psi, min | 47 (AF) | 97 (AF) | 13 (AF) | 51 (AF) | 58 (AF) | 55 (AF) |
| 180 Peel, SS lb/in | 3.2 (AF) | 4.7 (AF) | 3.7 (AF) | 3.2 (AF) | 2.6 (AF) | 4.3 (CF) |

Example 4(C) contained two separate processes to make silicone-acrylic hybrid PSA: (1) making acrylic polymer, (2) making acrylic-silicone polymer and then followed by making silicone-acrylic hybrid PSA in the same reactor. Example 6(C) showed that hexamethyldisilizane did not effectively neutralize KOH and thus the final solution gelled in less than 6 months. Example 7(C) and 8(C) demonstrated that the basicity of NH$_4$OH(aq) and (NH$_4$)$_2$CO$_3$ were not strong enough to make a single-phase silicone-acrylic hybrid PSA. Example 9 showed that one-pot process using with KOH as the catalyst led to a stable and one phase silicone-acrylic hybrid PSA after neutralization. Example 10 showed that the one-pot process was robust: a change of the procedure by adding silicone polymer before acrylic polymerization still led to a stable and one-phase silicone-acrylic hybrid PSA. The PSA properties were not affected by the process, but contributes to the ratio of components of acrylic polymer and silicone polymers, as the ratio contributes to the overall shear and peel strength of the PSA.

Figure 1:
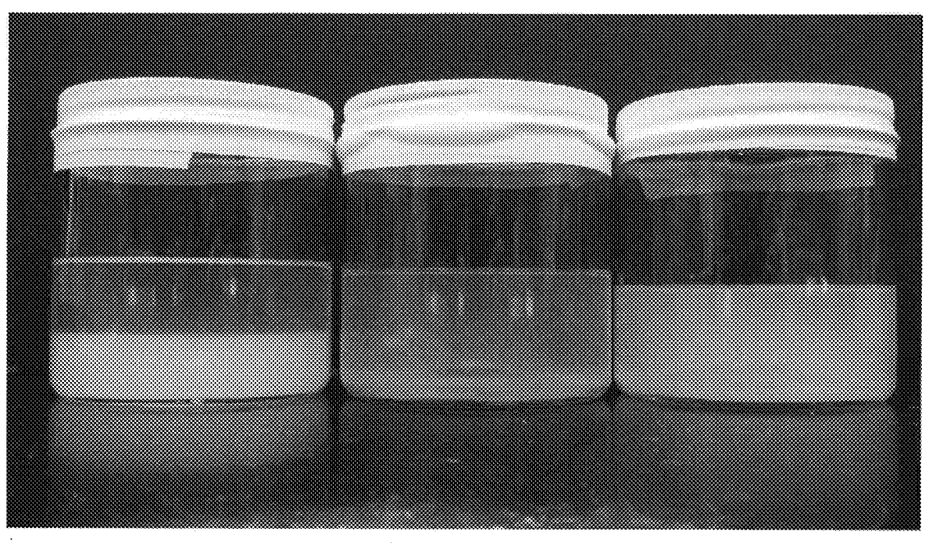
FIG. 1 a set of three photograph of various silicone-acrylic hybrid PSA solutions.

FIG. 1 is a photograph of Examples 2(C), 9, and 10 photographed with a Canon PowerShot SX40 HS, 12.1 Mega Pixels after aging for over six months. Example 2(C) has phase separated, whereas Examples 9 and 10, made with the inventive one-pot method, remained as a homogeneous single phase even after aging for six months.

Many modifications and variations of this invention can be made without departing from its spirit and scope, as will be apparent to those skilled in the art. The specific embodiments described herein are offered by way of examples only, and the invention is to be limited only by the terms of the appended claims, along with the full scope of equivalents to which such claims are entitled.

I claim:
1. A one-pot process of making a single-phase silicone-acrylic hybrid composition comprising the steps of:
  (a) making an acrylic polymer solution by a free radical polymerization in an organic solution;
  (b) adding (i) a silicone polymer and (ii) a catalyst to the acrylic polymer solution and reacting to form a silicone-acrylic hybrid solution;
  (c) neutralizing the silicone-acrylic hybrid solution with a neutralization reagent,
  (d) filtering any solid precipitates from the silicone-acrylic hybrid solution to form a single-phase silicone acrylic hybrid composition in solution;
  wherein the ratio of the silicone polymer and the acrylic polymer is from 50:1 to 1:50,
  wherein the silicon-acrylic hybrid composition comprises —Si—O—Si— covalent bond linkages between the silicone polymer and the acrylic polymer;
  wherein the one-pot process is conducted in a single reaction setting; and
  wherein the silicon-acrylic hybrid composition remains as a single-phase for over six months.
2. A one-pot process of making a single-phase silicone-acrylic hybrid composition comprising the steps of:
  (a) making an acrylic polymer solution by polymerizing:
    (i) a mixture of monomers, wherein at least one monomer comprises a hydrolyzable silane (meth)acrylic monomer and/or a siloxane (meth)acrylic macromer,
    (ii) a free radical initiator,
    (iii) an organic solvent,
  wherein the reaction temperature is from about 50 to about 150° C., and reaction time is from about 2 to 24 hr;
  (b) adding (i) a silicone polymer, and (ii) a catalyst into the acrylic polymer solution (a) and reacting at a reaction temperature of about 50 to about 150° C. for about 2 to 24 hours to form a silicone-acrylic hybrid solution;
  (c) neutralizing the silicone-acrylic hybrid solution at a temperature of about room temperature to about 150° C. for about 2 to 24 hours; and
  (d) filtering any solid precipitates from the silicone-acrylic hybrid solution to form a single-phase silicone acrylic hybrid composition in solution;
  wherein the ratio of the silicone polymer and the acrylic polymer is from 50:1 to 1:50, wherein the silicon-acrylic hybrid composition comprises —Si—O—Si— covalent bond linkages between the silicone polymer and the acrylic polymer;

wherein the one-pot process is conducted in a single reaction setting; and wherein the silicon-acrylic hybrid composition remains as a single-phase for over six months.

3. The one-pot process of claim 1, wherein the step (a) making of acrylic polymer is formed in the presence of the silicone polymer (b)(i).

4. The one-pot process of claim 2 wherein the hydrolyzable silane (meth)acrylic monomer and/or the siloxane (meth)acrylic macromer is in the content of about 0.1 to about 50 wt % based on the total weight of acrylic monomers.

5. The one-pot process of claim 2, wherein the hydrolyzable silane (meth)acrylic monomer (a)(i) has a formula of CH$_2$=CHR'COO—X—SiR"$_{n-3}$Y$_n$, wherein R' is H or methyl group; R" is selected from the group consisting of alkyl, aryl, fluoroalkyl, trialkylsilyl, triarylsilyl, vinyl, or combination thereof;

X is a linear, cyclic, or branched divalent link selected from the group of alkylene, arylene, oxyalkylene, oxyarylene, ester, amine, glycol, imide, amide, alcohol, carbonate, urethane, urea, sulfide, ether, or a derivative or combination thereof; and Y is selected from the hydrolyzable group consisting of alkoxy, aryloxy, acetoxy, oximino, enoxy, amino, amido, α-hydroxycarboxylic acid amide (—OCR'$_2$CONR"2), α-hydroxycarboxylic acid ester (—OCR'2COOR"), H, halogen, or combination thereof; n is selected from 1, 2, and 3.

6. The one-pot process of claim 4, wherein the siloxane (meth)acrylic macromer (a)(i) is a mono(meth)acrylate terminated polydimethylsiloxane polymer or oligomer.

7. The one-pot process of claim 2, wherein the monomers (a)(i) further comprises a second monomer that has a formula of CH$_2$=CR$^1$R$^2$, wherein R$^1$ is H or methyl group;

R$^2$ is selected from the group consisting of COOR$^3$, OCOR$^3$, aryl, heterocyclic, or combination thereof;

R$^3$ is selected from the group consisting of H, alkyl, aryl, allyl, fluoroalkyl, hydroxyalkyl, trialkylsilyl, triarylsilyl, epoxyalkyl, aminoalkyl, ammoniumalkyl or combination thereof.

8. The one-pot process of claim 7, wherein the second monomer is selected from the group consisting of methyl (meth)acrylate, ethyl (meth)acrylate, butyl (meth)acrylate, 2-ethylhexyl (meth)acrylate, isooctyl (meth)acrylate, t-octyl (meth)acrylamide, hydroxyethyl (meth)acrylate, hydroxypropyl (meth)acrylate, 2-(ciimethylamino)ethyl (meth)acrylate, [2-(acryloyloxy)ethyl]trimethylammonium, (meth)acrylic acid, 2-carboxyethyl acrylate, vinyl acetate, 1-vinyl-2-pyrrolidinone, styrene, α-methylstyrene, or combination thereof.

9. The one-pot process of claim 2, wherein the radical initiator (a)(ii) is selected from the group consisting of 2,2'-azobisisobutyronitrile, 1,1'-azobis(cyclohexanecarbonitrile), 2,2'-azodi(2-methylbutyronitrile), 4,4-azobis(4-cyanovaleric acid), 1,1'-azobis(cyanocyclohexane), 2-2'-Azobis (2,4-dimethylvaleronitrile), 2,2-bis(tert-butylperoxy)butane, test-amyl peroxypivalate, cyclohexanone peroxide, benzoyl peroxide, or combination thereof.

10. The one-pot process of claim 2, wherein the organic solvent (a)(iii) is selected from the group consisting of aliphatic hydrocarbons, aromatic hydrocarbon, ether, ketone, alcohol, alkyl acetate, tetrahydrofuran, water and mixtures thereof.

11. The one-pot process of claim 1, wherein the (b)(i) silicone polymer is a siloxane polymer, a silicone resin, or combination of the two with a ratio range from about 9:1 to 1:9.

12. The one-pot process of claim 11, wherein the siloxane polymer is a diorganosubstituted polysiloxane that has terminal group selected from hydrolyzable hydroxyl, alkoxy hydride, or combination thereof.

13. The one-pot process of claim 11, wherein the siloxane polymer has weight average molecular weight of from about 100 g/mol to 3,000,000 g/mol.

14. The one-pot process of claim 11, wherein the silicone resin comprises at least one tetrafunctional siloxyl unit SiO$_{4/2}$ and at least one triorganosiloxy unit R$_3$SiO$_{1/2}$, wherein the R is methyl, hydroxyl, vinyl, phenyl, (meth)acryloxy, or combination thereof, and the mole ratio of the units SiO$_{4/2}$ to R$_3$SiO$_{1/2}$ is from 1:2 to 2:1; wherein the R is from about 0.05 wt % to 10 wt % based on the total weight of the silicone resin.

15. The one-pot process of claim 14, wherein the silicone resin has weight average molecular weight of from about 100 g/mol to 3,000,000 g/mol.

16. The one-pot process of claim 2, wherein the (b)(ii) catalyst has a pKa value of ≤6 or ≥15.

17. The one-pot process of claim 16, wherein catalyst is selected from MOR, wherein M is Cs, Rb, K, Na, Li and R is H, alkyl, aryl, allyl, fluoroalkyl, or combination thereof; organolithium reagents, Grignard reagents, methanesulfonic acid, sulfuric acid, acidic clay, Lewis acid, acidic ion exchange resins, or combination thereof.

18. The one-pot process of claim 1, wherein the neutralization reagent is selected from dilute hydrochloric acid (aq), chlorotrimethylsilane, fume silica, sodium carbonate, sodium bicarbonate, calcium carbonate, acetic acid, ammonium hydroxide(aq), ammonium carbonate, hexamethyldisilazane, aminopropyltrimethylsilane, propylene epoxide, carbon dioxide gas or combination thereof.

19. The one-pot process of claim 1, further comprising step (e) adding an additive to the silicone-acrylic hybrid pressure sensitive adhesive composition, wherein the additive is selected from the group consisting of tackifiers, additional polymers, silicon oils, plasticizers, diluents, solubilizing agents, organic or inorganic fillers, pigments, fluorescent additives, flow and leveling additives, wetting agents, surfactants, antifoaming agents, rheology modifiers, emulsifiers, humectants, gelling agent, colorants, other surface modifying agents, fragrances, permeation enhancers, stabilizers, antioxidants, and combination thereof.

20. A process for making a transdermal device comprising a silicone-acrylic hybrid pressure sensitive adhesive (PSA) composition and an active in a one-pot process comprising the steps of:

(a) making an acrylic polymer by a polymerization reaction of (i) a mixture of monomers, wherein at least one monomer comprises a hydrolyzable silane (meth)acrylic monomer and/or a siloxane (meth)acrylic macromer, (ii) a radical initiator; (iii) an organic solvent, and (b) adding (i) a silicone polymer and (ii) a base or an acid catalyst into the acrylic polymer solution (a) and reacting at a temperature of about 50 to about 150° C. for about 2 to about 24 hours to form a silicone-acrylic hybrid solution;

(c) neutralizing the solution (b) at a temperature of about room temperature to about 150° C. for about 2 to 24 hours;
(d) removing any solid precipitates to form a single-phase silicone-acrylic hybrid PSA composition;
(e) adding the active to the solution (d), wherein the active is a pharmaceutical, nutraceutical and/or cosmeceutical agent;
(f) applying the solution (e) onto a film substrate; and
(g) evaporating the solvent to form a transdermal device
wherein the one-pot process is conducted in a single reaction setting; and
wherein the silicon-acrylic hybrid pressure sensitive adhesive composition remains as a single-phase for over six months.

* * * * *

UNITED STATES PATENT AND TRADEMARK OFFICE
CERTIFICATE OF CORRECTION

PATENT NO. : 11,919,990 B2
APPLICATION NO. : 17/060358
DATED : March 5, 2024
INVENTOR(S) : Yuxia Liu Page 1 of 1

It is certified that error appears in the above-identified patent and that said Letters Patent is hereby corrected as shown below:

In the Claims

Column 19, Line 53 change "2-(ciimethylamino)ethyl (meth) acrylate" to --2-(dimethylamino)ethyl (meth) acrylate--.

Signed and Sealed this
Second Day of September, 2025

Coke Morgan Stewart
*Acting Director of the United States Patent and Trademark Office*